(12) United States Patent
Acharya et al.

(10) Patent No.: US 12,018,972 B2
(45) Date of Patent: Jun. 25, 2024

(54) CONTACTLESS WASTE TANK LEVEL SENSING SYSTEMS AND METHODS

(71) Applicant: B/E Aerospace, Inc., Winston Salem, NC (US)

(72) Inventors: Pradeep Acharya, Bangalore (IN); Sreekanth Koti Ananda Rao, Bangalore (IN); Shyam Kumar Dattatri, Bangalore (IN)

(73) Assignee: B/E AEROSPACE, INC., Winston Salem, NC (US)

( * ) Notice: Subject to any disclaimer, the term of this patent is extended or adjusted under 35 U.S.C. 154(b) by 92 days.

(21) Appl. No.: 17/846,387

(22) Filed: Jun. 22, 2022

(65) Prior Publication Data

US 2023/0160736 A1  May 25, 2023

(30) Foreign Application Priority Data

Nov. 24, 2021  (IN) .............................. 202141054169

(51) Int. Cl.
| | |
|---|---|
| *G01F 23/292* | (2006.01) |
| *B64D 11/02* | (2006.01) |
| *G01N 33/487* | (2006.01) |
| *G01S 17/88* | (2006.01) |

(52) U.S. Cl.
CPC .......... *G01F 23/2921* (2013.01); *B64D 11/02* (2013.01); *G01N 33/4875* (2013.01); *G01S 17/88* (2013.01)

(58) Field of Classification Search
CPC . G01F 23/2921; B64D 11/02; G01N 33/4875; G01S 17/88
See application file for complete search history.

(56) References Cited

U.S. PATENT DOCUMENTS

| | | |
|---|---|---|
| 3,995,328 A | 12/1976 | Carolan et al. |
| 8,185,977 B2 | 5/2012 | Seibt |
| 8,424,130 B2 | 4/2013 | Dannenberg et al. |
| 8,806,946 B2 | 8/2014 | Flister et al. |
| 10,266,268 B2 | 4/2019 | Boodaghians et al. |
| 10,352,755 B2 | 7/2019 | Truong et al. |
| 10,935,413 B2 | 3/2021 | Chan et al. |
| 11,064,886 B2 | 7/2021 | Prokopp |
| 11,091,903 B2 | 8/2021 | Grover et al. |
| 2013/0232677 A1 | 9/2013 | Miller et al. |
| 2018/0364088 A1* | 12/2018 | Philipp ................ B60K 15/061 |
| 2020/0191580 A1* | 6/2020 | Christensen ......... G01C 21/343 |
| 2022/0204373 A1* | 6/2022 | Jensen .................... G01S 17/88 |

FOREIGN PATENT DOCUMENTS

| | | | |
|---|---|---|---|
| CN | 112645505 | 4/2021 | |
| FR | 3061285 B1 * | 8/2019 | ............ G01B 11/00 |
| WO | 2020180673 | 9/2020 | |
| WO | 2020190301 | 9/2020 | |

OTHER PUBLICATIONS

European Patent Office, European Search Report dated Apr. 3, 2023 in Application No. 22209090.4.

\* cited by examiner

*Primary Examiner* — Andrew W Bee
(74) *Attorney, Agent, or Firm* — SNELL & WILMER L.L.P.

(57) ABSTRACT

A system may comprise: a contactless sensor configured to couple to a waste tank; a controller electronically coupled to the contactless sensor, the controller configured to: receive, via the contactless sensor, a waste water level data from the contactless sensor, calculate a waste water level based on the waste water level data.

17 Claims, 4 Drawing Sheets

CONTACTLESS WASTE TANK LEVEL SENSING SYSTEMS AND METHODS

CROSS-REFERENCE TO RELATED APPLICATIONS

This application claims priority to, and the benefit of, India Patent Application No. 202141054169, filed Nov. 24, 2021 (DAS Code 49AC) and titled "CONTACTLESS WASTE TANK LEVEL SENSING SYSTEMS AND METHODS," which is incorporated by reference herein in its entirety for all purposes.

FIELD

The present disclosure relates to drain systems and methods for improved waste tank level sensing and, more particularly, improved waste tank level sensing systems and methods for use in aircraft lavatories

BACKGROUND

Aircraft cabins include lavatories having drain systems disposed therein. Waste tank level sensing systems and methods may be prone to erroneous readings indicating a waste tank is in a full state when the waste tank is not. In this regard, an associated toilet may be inoperable during a period of time while the waste tank is deemed in the full state.

SUMMARY

A system is disclosed herein. The system may comprise: a contactless sensor configured to couple to a waste tank; a controller electronically coupled to the contactless sensor, the controller configured to: receive, via the contactless sensor, a waste water level data from the contactless sensor, calculate a waste water level based on the waste water level data.

In various embodiments, the system may further comprise a display device electronically coupled to the controller, the controller configured to send the waste water level to the display device. The system may further comprise the waste tank, wherein the waste tank is disposed on an aircraft. The system may further comprise an actuator electronically coupled to the controller, the controller configured to actuate the actuator in response to the controller determining the waste water level exceeded a level threshold. The actuator may be configured to lock a lavatory in an aircraft. The actuator may be configured to close a valve disposed between a toilet bowl and the waste tank. The contactless sensor may comprise a laser doppler sensor. The system may further comprise the waste tank and a transparent lens, the contactless sensor configured to transmit and receive a laser beam through the transparent lens, the transparent lens coupled to the waste tank.

A plumbing system for an aircraft is disclosed herein. The plumbing system may comprise: a waste tank; a toilet bowl; a fluid conduit extending from the waste tank to the toilet bowl; a valve at least partially disposed in the fluid conduit; and a contactless sensor coupled to the waste tank, the contactless sensor configured to emit a laser beam into the waste tank and receive a return signal of the laser beam to determine a waste water level in the waste tank.

In various embodiments, the plumbing system may further comprise a waste water level detection system comprising the contactless sensor, the waste water level detection system configured for rotatory motion of the contactless sensor. The plumbing system may further comprise a transparent lens coupled to the waste tank, the laser beam configured to travel through the transparent lens. The plumbing system may further comprise a controller in electronic communication with the contactless sensor, the controller configured to calculate the waste water level in the waste tank based on sensor data from the contactless sensor. The plumbing system may further comprise a display device electronically coupled to the controller, the display device configured to display the waste water level in the waste tank. The controller may be configured to send the waste water level in the waste tank to the display device. The plumbing system may further comprise an actuator electronically coupled to the controller, the controller configured to actuate the actuator in response to the controller determining a waste water level threshold has been exceeded. The actuator may be configured to at least one of lock a lavatory in the aircraft and close the valve.

An aircraft is disclosed herein. The aircraft may comprise: a waste tank; a contactless sensor coupled to the waste tank, the contactless sensor configured to emit a laser beam into the waste tank and receive a return signal of the laser beam to determine a waste water level in the waste tank; and a controller configured to receive data from the contactless sensor, the controller configured to determine a waste water level based on the data.

In various embodiments, the contactless sensor is a laser doppler sensor. The aircraft may further comprise a transparent lens coupled to the waste tank, the contactless sensor configured to emit the laser beam through the transparent lens. The contactless sensor may be disposed external to a cavity defined by the waste tank.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosures, however, may best be obtained by referring to the detailed description and claims when considered in connection with the drawing figures, wherein like numerals denote like elements.

DETAILED DESCRIPTION

The detailed description of exemplary embodiments herein refers to the accompanying drawings, which show exemplary embodiments by way of illustration and their best mode. While these exemplary embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Disclosed herein is waste water level detection systems and method for use in aircrafts. The waste water level detection system comprises a contactless sensor configured to emit a laser beam and receive a return signal from the laser beam within a waste tank to determine a waste water level within the waste tank. The waste water level detection system may reduce a part count of typical systems, increase accuracy relative to typical contact systems, and/or provide continuous monitoring, e, in accordance with various embodiments.

Figure 1:
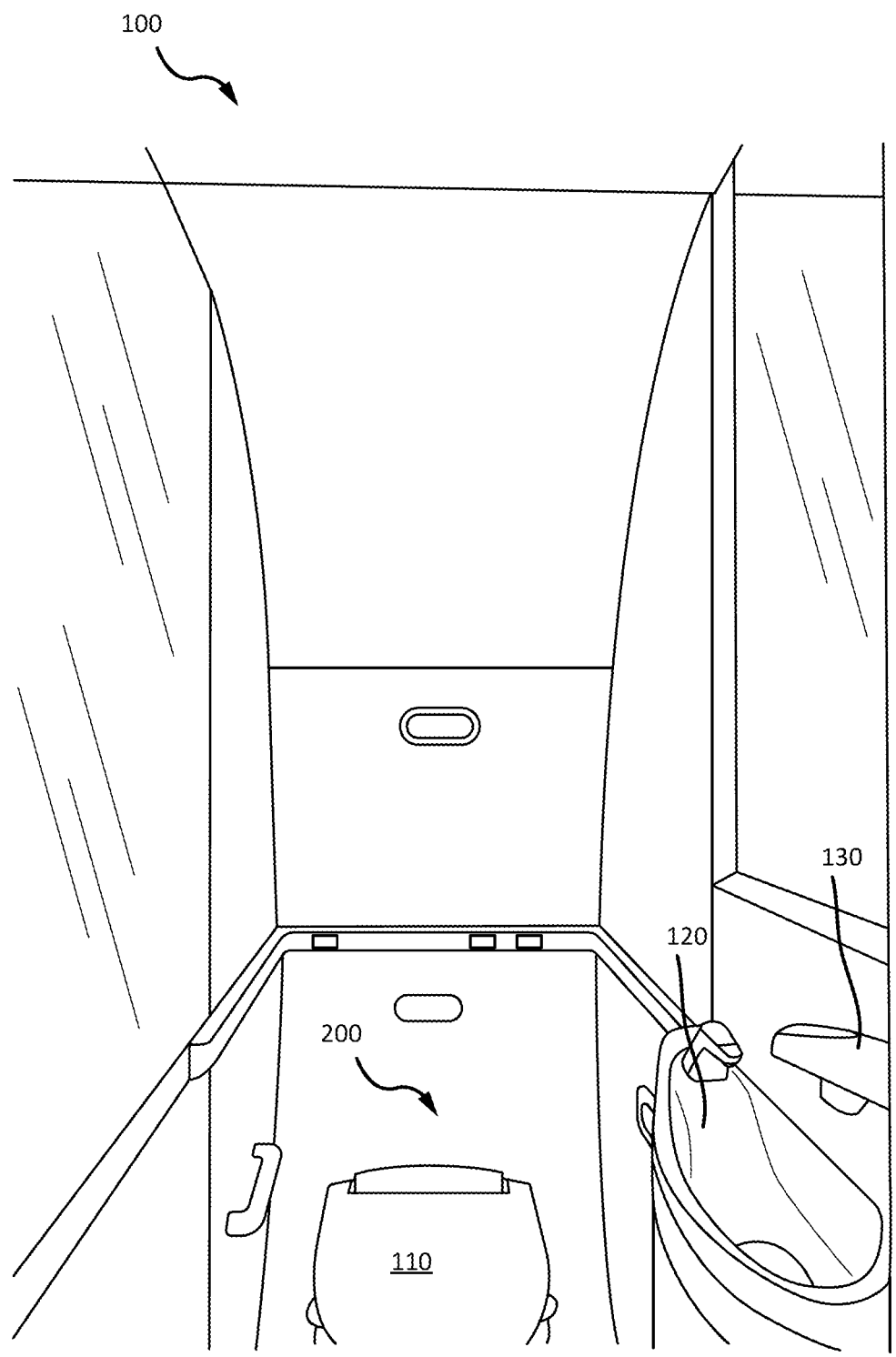
FIG. 1 illustrates a perspective view of a lavatory for an aircraft, in accordance with various embodiments.

Referring now to FIG. 1, a perspective view of a lavatory 100 of an aircraft is illustrated in accordance with various embodiments. The lavatory 100 comprises a toilet 110, a water basin 120 (e.g., a sink), and a faucet 130. In various embodiments, the lavatory 100 further comprises a plumbing system 200. The plumbing system 200 is in fluid communication with the toilet 110, the water basin 120, and the faucet 130. In this regard, in response to flushing the toilet 110, waste water may be transferred throughout the plumbing system 200 as described further herein. Similarly, in response to running water via the faucet 130, waste water may be transferred throughout the plumbing system 200 as described further herein.

Figure 2:
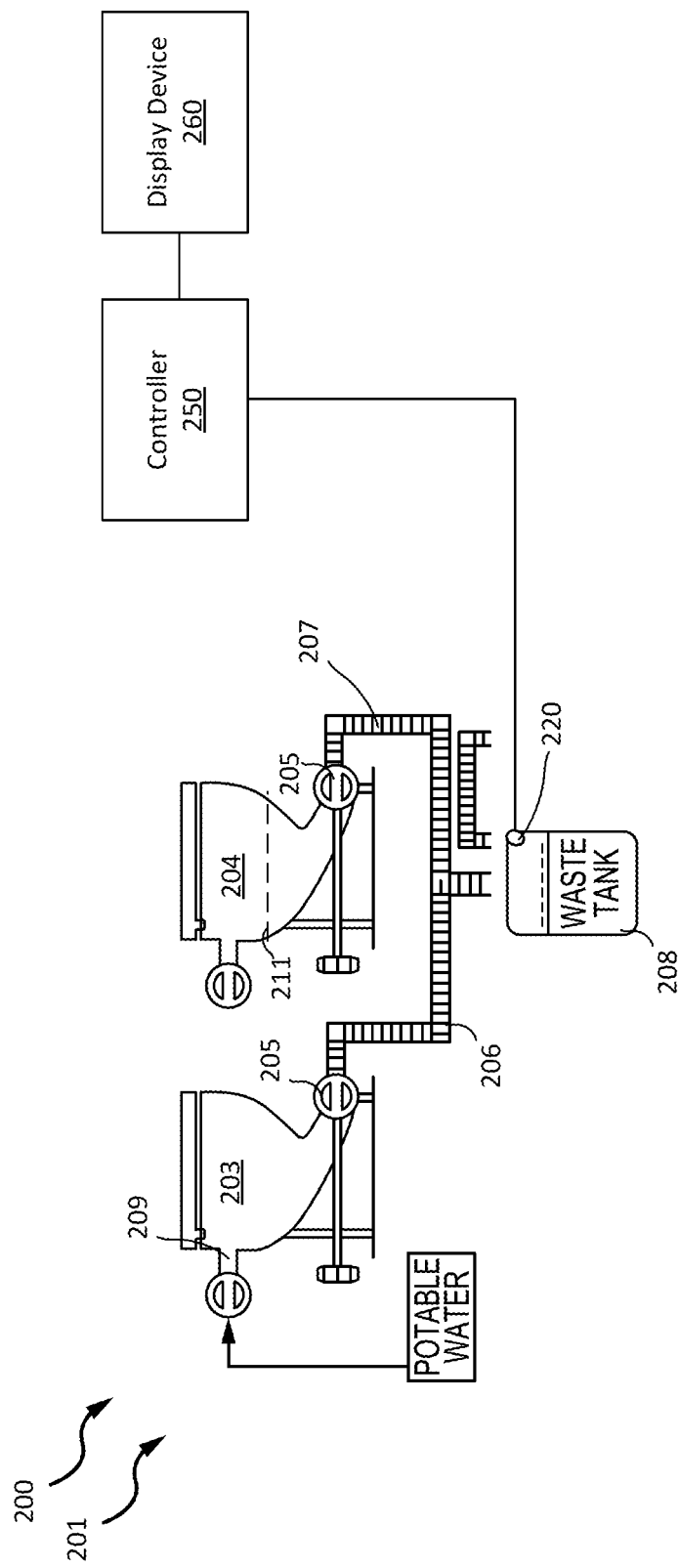
FIG. 2 illustrates a schematic view of a plumbing system for an aircraft, in accordance with various embodiments.

Referring now to FIG. 2, a plumbing system 200 comprising a waste water level detection system 201 is illustrated, in accordance with various embodiments. In various embodiments, the plumbing system 200 comprises a rinse valve 205 associated with each toilet bowl (e.g., toilet bowls 203, 204). The rinse valve 205 is configured to open in response to external activation (e.g., via flushing of a handle, via a sensor detecting a person is no longer in front of the sensor, or the like). In response to opening the rinse valve 205, waste water may flow (e.g., via fluid conduits 206, 207) from the toilet bowl (e.g., toilet bowl 203 or toilet bowl 204) to a waste tank 208. In various embodiments, during the flushing process, potable water may be dispensed through a potable water port 209 disposed in each toilet bowl (e.g., toilet bowls 203, 204). In this regard, any solid waste may be transported from the toilet bowl (e.g., toilet bowl 203 or toilet bowl 204) to the waste tank 208 as waste water, in accordance with various embodiments.

In various embodiments, a contactless sensor 220 is coupled to the waste tank 208. As described further herein, the contactless sensor 220 may be disposed within the waste tank 208, coupled to an external surface of the waste tank 208, or the like. The present disclosure is not limited in this regard. The contactless sensor 220 is in electronic communication with the controller 250.

In various embodiments the contactless sensor 220 is in electronic (i.e., electrical or wireless) communication with a controller 250. In various embodiments, controller 250 may be integrated into computer system of the aircraft. In various embodiments, controller 250 may be configured as a central network element or hub to access various systems and components of the system 201. Controller 250 may comprise a network, computer-based system, and/or software components configured to provide an access point to various systems and components of the system 201. In various embodiments, controller 250 may comprise a processor. In various embodiments, controller 250 may be implemented in a single processor. In various embodiments, controller 250 may be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. Controller 250 may comprise a processor configured to implement various logical operations in response to execution of instructions, for example, instructions stored on a non-transitory, tangible, computer-readable medium configured to communicate with controller 250.

In various embodiments, the contactless sensor 220 comprises a laser doppler sensor. The contactless sensor 220 may be disposed proximate a top portion of the waste tank 208. In this regard, the waste tank 208 may continuously or periodically provide a waste water level in the waste tank 208 to the controller 250. Thus, in response to a waste level exceeding a predetermined threshold (e.g., 90% to 100% vertical height of the waste water level sensor), the controller 250 may send a signal to the display device 260 a waste tank full condition. Thus, the crew may be informed that the waste tank is full and appropriate actions may be taken. In various embodiments, the controller 250 may be configured to send a warning signal at a predetermined level (e.g., 80% vertical height of the waste water level sensor) to indicate the waste tank should be emptied soon (i.e., a waste tank near full condition signal).

Figure 3:
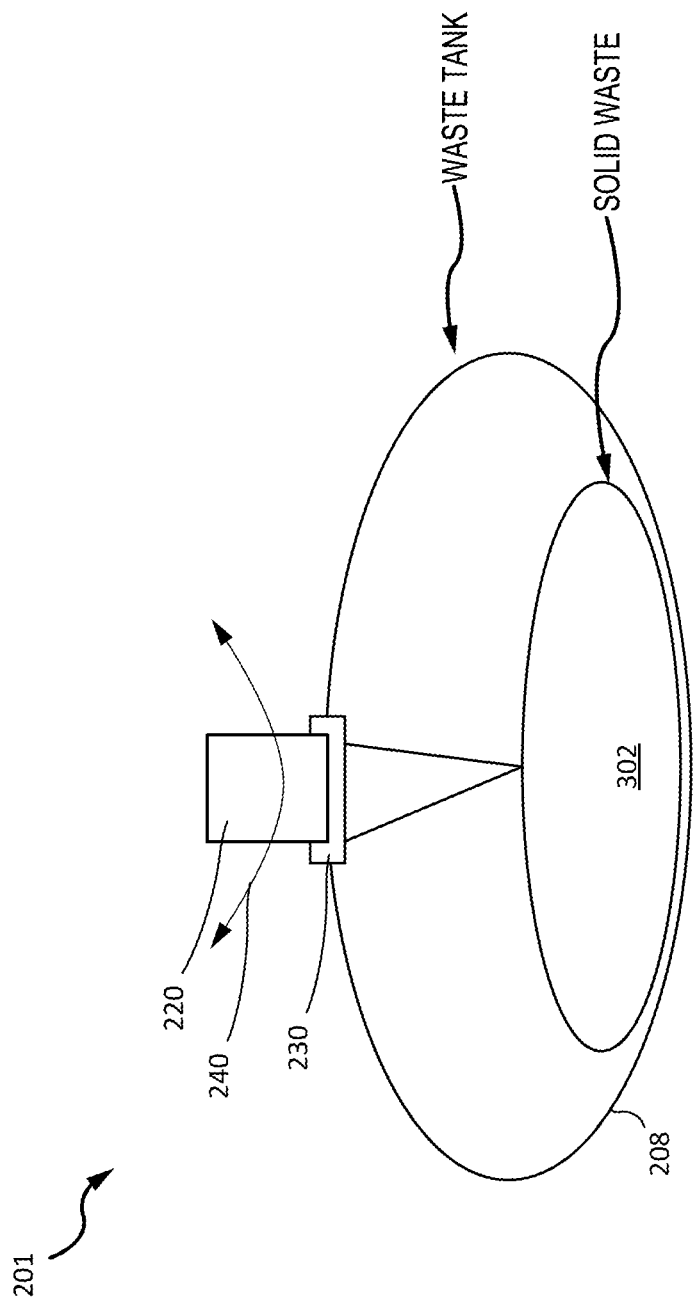
FIG. 3 illustrates a schematic view of a waste water level detection system, in accordance with various embodiments.

Referring now to FIG. 3, a schematic view of the waste water level detection system 201 is illustrated in accordance with various embodiments. The system 201 comprises the contactless sensor 220 coupled to the waste tank 208 of the plumbing system 200 from FIG. 2. In various embodiments, the contactless sensor 220 may be disposed external to the waste tank 220. For example, a transparent lens 230 may be disposed between a cavity defined by the waste tank 208 and the contactless sensor 220. In various embodiments, the transparent lens 230 is coupled to the waste tank 208 and the contactless sensor 220 is coupled to the transparent lens 230. Although illustrated with transparent lens 230, the present disclosure is not limited in this regard. For example, the contactless sensor 220 may be coupled directly to the waste tank 208 or disposed within the waste tank 208 and still be within the scope of this disclosure. Although illustrated as being coupled to the transparent lens 230, the present disclosure is not limited in this regard. For example, the contactless sensor 220 may be spaced apart from the transparent lens 230 to facilitate motion of the contactless sensor 220 during use, in accordance with various embodiments. In various embodiments, the transparent lens 230 may provide protection from waste water splash, or the like during operation of the plumbing system 200 from FIG. 2.

In various embodiments, the contactless sensor 220 comprises a transceiver. The transceiver is configured to emit a laser beam into the waste tank 208, receive a return signal of the laser beam, calculate a time from emitting the laser beam to receiving the return signal, and determine a height of waste water within the waste tank 208 based on the time and a speed of the laser beam.

In various embodiments, the waste water level detection system 201 is configured to facilitate rotary motion 240 of the contactless sensor 220 (e.g., via a ball and socket joint, or the like) to allow the contactless sensor 220 to obtain various data points within the waste tank 208 and/or map a waste water profile within the waste tank 208.

In various embodiments, the contactless sensor 220 may prevent any erroneous readings due to clogging of waste from contact sensors (e.g., point level sensors). Additionally, in various embodiments, as multiple contact sensors are typically used for waste water level detection, the contactless sensor 220 may reduce a sensor count from multiple to one, in accordance with various embodiments.

In various embodiments, the contactless sensor 220 may provide continuous waste water level data to the controller 250. In this regard, the controller 250 may be configured to send the waste water level data to the display device 260 to be displayed to any member of the cabin crew. Thus, the waste water level may be continuously monitored, in accordance with various embodiments.

Figure 4:
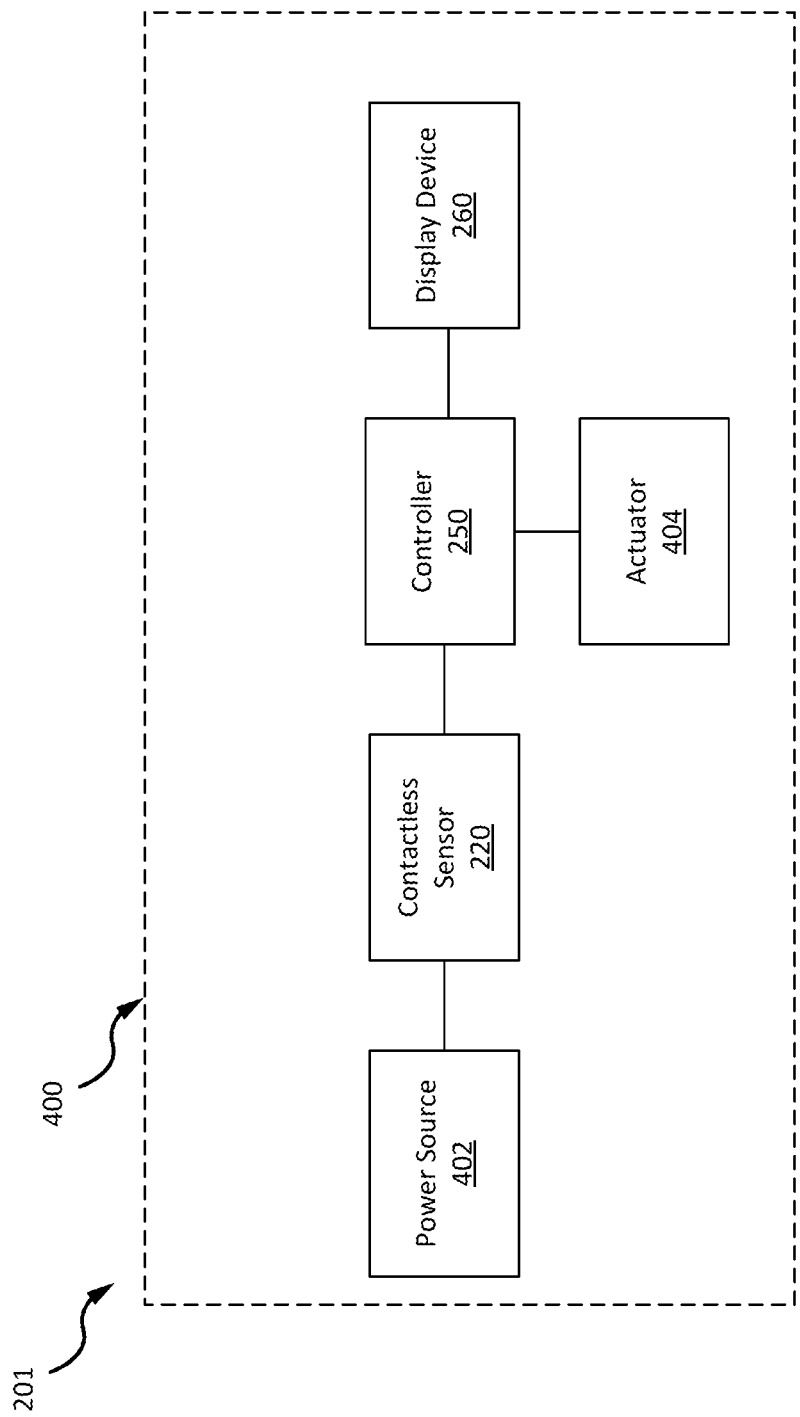
FIG. 4 illustrates a schematic view of a control system for a waste water level detection system, in accordance with various embodiments.

Referring now to FIG. 4, a schematic view of a control system 400 for the system 201 from FIGS. 2 and 3. In various embodiments, the control system 400 comprises the controller 250, the contactless sensor 220, a power source 402, and the display device 260. The power source 402 may be electrically coupled, and configured to power, the contactless sensor 220. In various embodiments, the power source is a battery, or any other power source disposed on an aircraft. The present disclosure is not limited in this regard.

In various embodiments, the control system 400 further comprises an actuator 404 electronically (e.g., via a wired connection or wireless connection) the controller 250. In this regard, in response to the controller 250 determining the waste tank 208 from FIGS. 2 and 3 is full, the controller 250 may actuate the actuator 404 to lock a respective lavatory, close a respective valve 205, or the like. In this regard, a lavatory, or toilet may be decommissioned in response to the waste tank 208 for the respective lavatory or toilet being filled.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system, comprising:
   a waste level detection system comprising a ball and socket joint and a contactless sensor, the contactless sensor configured to couple to a waste tank via the ball and socket joint;
   a controller electronically coupled to the contactless sensor, the controller configured to:
   receive, via the contactless sensor, a waste water level data from the contactless sensor,
   rotate, via the ball and socket joint, the contactless sensor to allow the contactless sensor to obtain various data points within the waste tank, and
   map a waste water profile based on the waste water level data.

2. The system of claim 1, further comprising a display device electronically coupled to the controller, the controller configured to send the waste water profile to the display device.

3. The system of claim 1, further comprising the waste tank, wherein the waste tank is disposed on an aircraft.

4. The system of claim 1, further comprising an actuator electronically coupled to the controller, the controller configured to actuate the actuator in response to the controller determining the waste water profile exceeded a level threshold.

5. The system of claim 4, wherein the actuator is configured to lock a lavatory in an aircraft.

6. The system of claim 4, wherein the actuator is configured to close a valve disposed between a toilet bowl and the waste tank.

7. The system of claim 1, further comprising the waste tank and a transparent lens, the contactless sensor configured to transmit and receive a laser beam through the transparent lens, the transparent lens coupled to the waste tank.

8. A plumbing system for an aircraft, comprising:
a waste tank;
a toilet bowl;
a fluid conduit extending from the waste tank to the toilet bowl;
a valve at least partially disposed in the fluid conduit; and
a waste water level detection system comprising a contactless sensor and a ball and socket joint, the ball and socket joint coupled to the waste tank, the contactless sensor coupled to the ball and socket joint, the contactless sensor configured to emit a laser beam into the waste tank and receive a return signal of the laser beam to determine a waste water level in the waste tank, the waste water level detection system configured to facilitate rotatory motion, via the ball and socket joint, of the contactless sensor to allow the contactless sensor to obtain various data points within the waste tank and map a waste water profile within the waste tank.

9. The plumbing system of claim 8, further comprising a transparent lens coupled to the waste tank, the laser beam configured to travel through the transparent lens.

10. The plumbing system of claim 8, further comprising a controller in electronic communication with the contactless sensor, the controller configured to calculate the waste water level in the waste tank based on sensor data from the contactless sensor.

11. The plumbing system of claim 10, further comprising a display device electronically coupled to the controller, the display device configured to display the waste water level in the waste tank.

12. The plumbing system of claim 11, wherein the controller is configured to send the waste water level in the waste tank to the display device.

13. The plumbing system of claim 10, further comprising an actuator electronically coupled to the controller, the controller configured to actuate the actuator in response to the controller determining a waste water level threshold has been exceeded.

14. The plumbing system of claim 13, wherein the actuator is configured to at least one of lock a lavatory in the aircraft and close the valve.

15. An aircraft, comprising:
a waste tank;
a waste level detection system comprising a ball and socket joint and a contactless sensor, the ball and socket joint coupled to the waste tank, the contactless sensor coupled to the ball and socket joint, the contactless sensor configured to emit a laser beam into the waste tank and receive a return signal of the laser beam to determine a waste water level in the waste tank, the waste level detection system configured to facilitate rotatory motion, via the ball and socket joint, of the contactless sensor to allow the contactless sensor to obtain various data points within the waste tank and map a waste water profile within the waste tank; and
a controller configured to receive data from the contactless sensor, the controller configured to determine the waste water profile based on the data.

16. The aircraft of claim 15, further comprising a transparent lens coupled to the waste tank, the contactless sensor configured to emit the laser beam through the transparent lens.

17. The aircraft of claim 15, wherein the contactless sensor is disposed external to a cavity defined by the waste tank.

* * * * *